United States Patent [19]

Levine

[11] 4,154,533

[45] May 15, 1979

[54] METHOD AND APPARATUS FOR MEASURING A CHARACTERISTIC OF FLOWING MATERIAL

[75] Inventor: Walter E. Levine, Port Huron, Mich.

[73] Assignee: Bindicator Company, Port Huron, Mich.

[21] Appl. No.: 812,186

[22] Filed: Jul. 1, 1977

[51] Int. Cl.² .......................................... G01N 21/48
[52] U.S. Cl. ..................................... 356/445; 250/574
[58] Field of Search ...................... 356/209, 211, 212; 250/564, 565, 573, 574, 576

[56] References Cited

U.S. PATENT DOCUMENTS

| | | | |
|---|---|---|---|
| 3,328,587 | 6/1967 | Brown et al. | 356/186 |
| 3,549,263 | 12/1970 | Osawa et al. | 356/209 |
| 3,776,642 | 12/1973 | Anson et al. | 356/212 |

Primary Examiner—John K. Corbin
Assistant Examiner—R. A. Rosenberger
Attorney, Agent, or Firm—Barnes, Kisselle, Raisch & Choate

[57] ABSTRACT

A method and apparatus for sampling and optically measuring a selected characteristic of flowing particulate material in which a shelf plate projects transversely into the material stream to collect and hold stationary thereon a quantity of material in the form of pile having an inclined surface exposed at an angle of repose with respect to the plate and over which additional material may flow. After a selected number of optical readings of material flowing over the angled surface, the shelf plate is momentarily partially withdrawn from the material stream such that previously-collected material spills therefrom, and then the plate is returned to the material stream so that fresh material is collected adjacent the material surface.

26 Claims, 11 Drawing Figures

U.S. Patent   May 15, 1979   Sheet 3 of 4   4,154,533
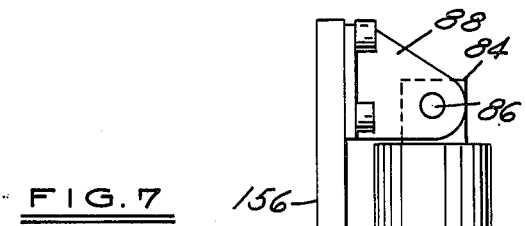
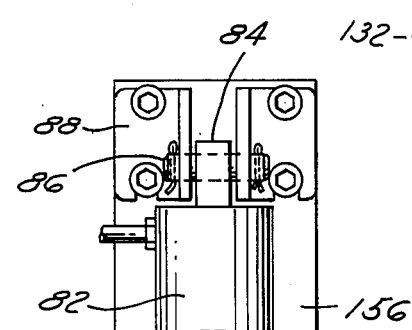
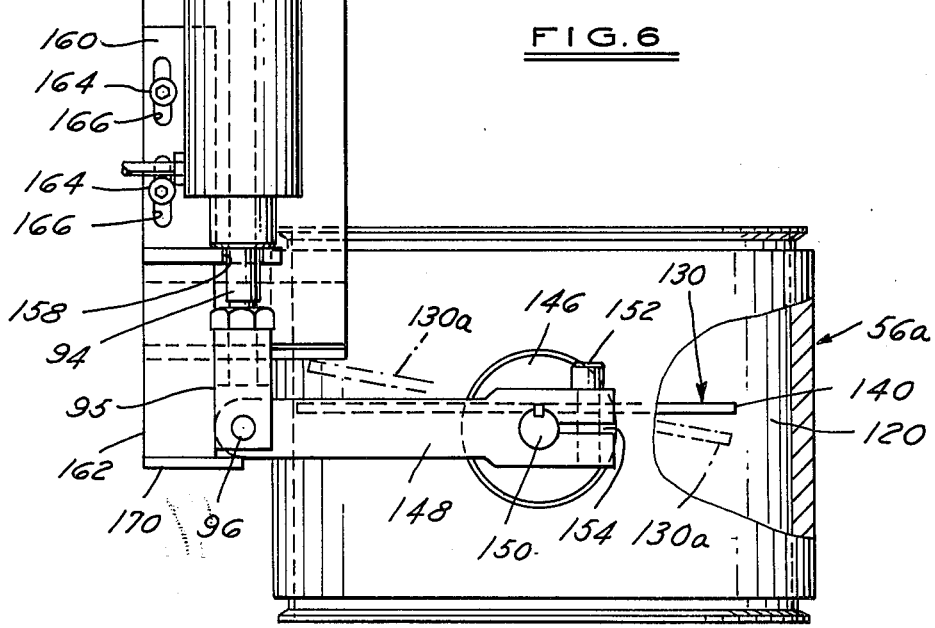

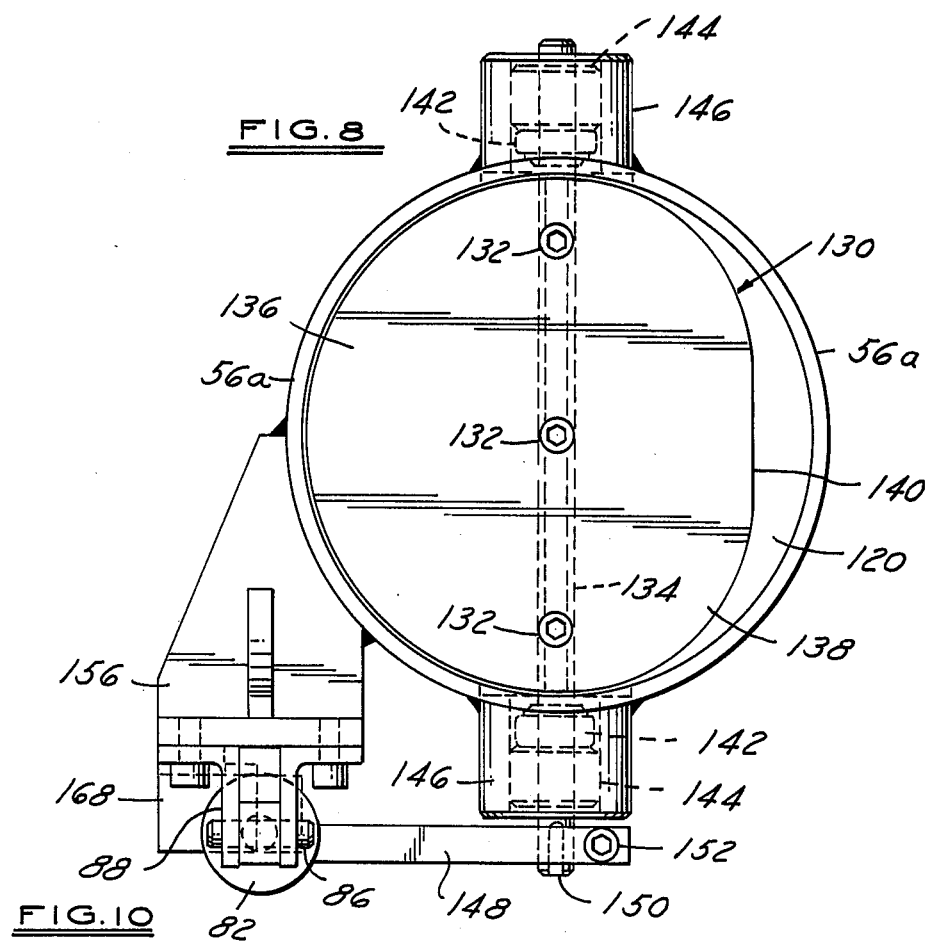
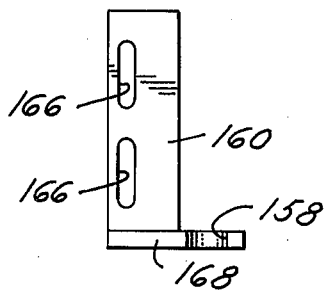
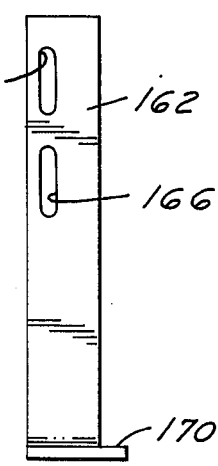

METHOD AND APPARATUS FOR MEASURING A CHARACTERISTIC OF FLOWING MATERIAL

The present invention relates to optical test methods and apparatus and, more particularly, to methods and apparatus for measuring a preselected characteristic of test materials, such as the moisture content thereof, using optical reflection/absorption techniques.

Typical prior art techniques for measuring moisture content of food products contemplate manually removing a test sample from the material bulk, weighing the sample, and then drying and reweighing the sample, the intervening weight loss being considered indicative of starting moisture content. Application of optical testing techniques in the food industry, as typified by the disclosures of U.S. Pat. No. 3,776,642 and No. 3,861,788, have commonly retained the requirement for manual sampling, and thus have failed to overcome the problems of expense and variations in sampling methods inherent therein. Moreover, it has been found that certain types of bulk food products which must be dried prior to packaging, such as kibbled or pelletized pet food for example, exit the process drier with an uneven moisture distribution within the individual pellets, i.e., with a damp central core surrounded by an over-dried outer shell. Although this uneven moisture distribution presents no particular difficulties with respect to the product itself because the moisture will assume a more even distribution with time after the product has been packaged, such distribution renders difficult the measurement, and particularly the continuous measurement, of product moisture content at or near the drier output as is desirable to effect close control of the drying process.

It is a general object of the present invention to provide a method and apparatus for use in optically measuring a selected characteristic of materials which obviate some or, preferably, all of the above-described disadvantages associated with and inherent in prior art techniques.

More specifically, it is an object of the present invention to provide a method and apparatus of the described type which is adapted for use in a food processing line on a continuous basis and/or which is particularly well adapted for accurately measuring the moisture content of pelletized food products having an uneven moisture distribution within the individual pellets.

It is another object of the present invention to provide a method and apparatus for measuring a preselected characteristic of flowing particulate materials which may be operated selectively on either a continuous or batch sampling basis.

The invention, together with additional objects, features and advantages thereof, will be best understood from the following description when read in conjunction with the accompanying drawings in which:

FIG. 1 is a fragmentary elevational view, partially sectioned, of a presently preferred embodiment of the invention connected to a bulk material screw conveyor;

FIGS. 2 and 3 are sectional views respectively taken along the lines 2—2 and 3—3 in FIG. 1;

FIG. 6 is an elevational view of an alternative embodiment of the invention.

FIG. 7 is a fragmentary side elevational view of the embodiment of FIG. 6;

FIG. 8 is a plan view of the embodiment of FIG. 6;

FIGS. 9 and 10 are elevational views of respective stop brackets employed in the embodiment of FIG. 6; and FIG. 11 is a bottom view of the stop bracket illustrated in FIG. 10.

Figures 1, 2, 3:
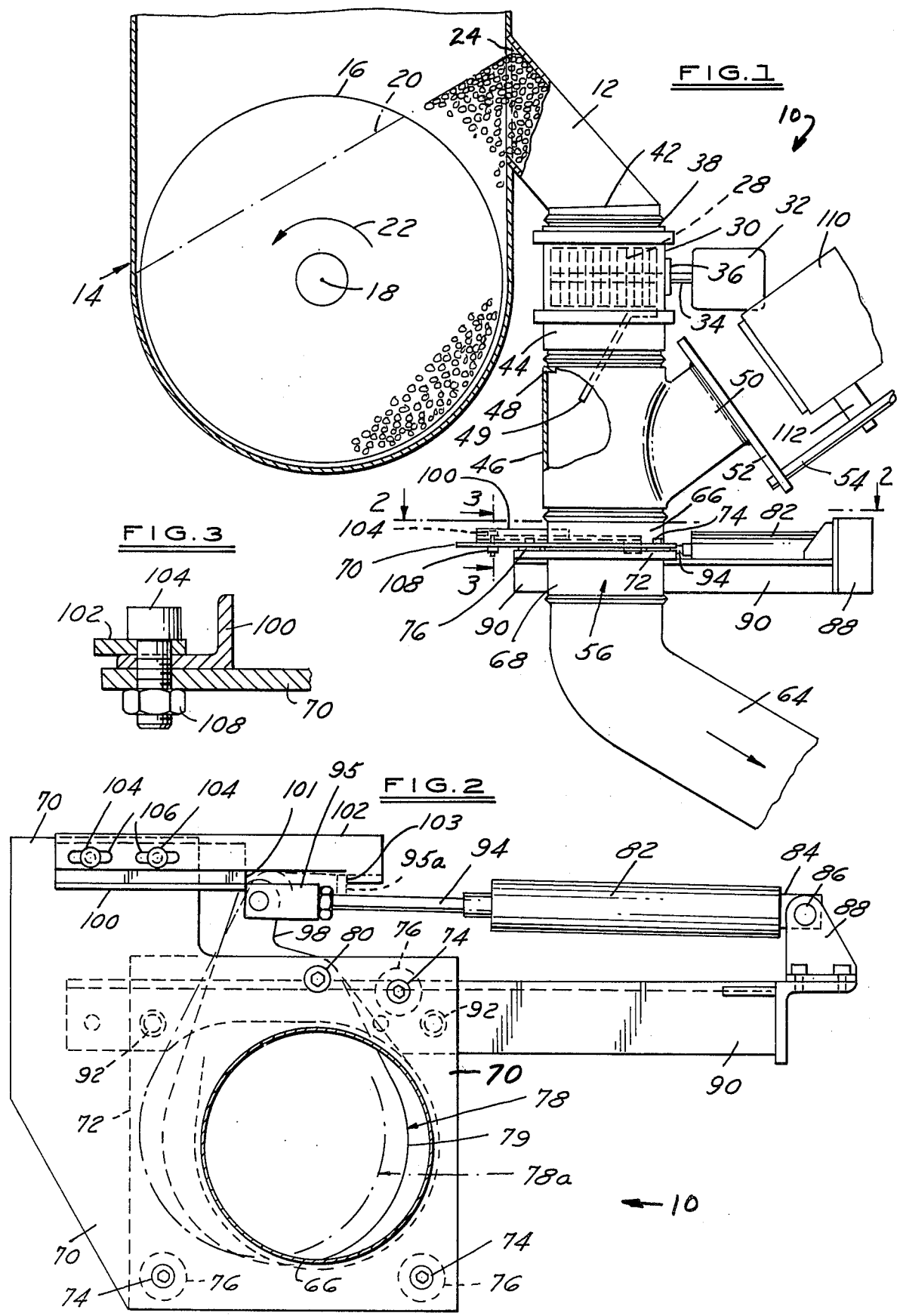

Referring to the drawings, FIG. 1 illustrates a preferred embodiment 10 of the invention connected by an angulated cylindrical conduit 12 to a bulk material conveyor 14 having a conveyor screw 16 which rotates about its axis 18 to propel material in the direction of its axis in the usual and well-known manner. The upper surface 20 of bulk material in conveyor 14 assumes a generally angulated position when screw 16 rotates counterclockwise as shown at 22, the mouth or entrance 24 of conduit 12 being disposed above screw axis 18 to receive only material near the uppermost portion of surface 20. This location of conduit input 24 has the advantage of preventing dust or small particles in the bulk material stream, which ordinarily collect near the bottom of the conveyor line and which may not possess a representative moisture content, for example, from entering conduit 12. Conduit 12 may be connected to receive material from a point in the conveyor line at or near the output of the material drier (not shown) for close supervision and control of the drying process.

Figure 4:
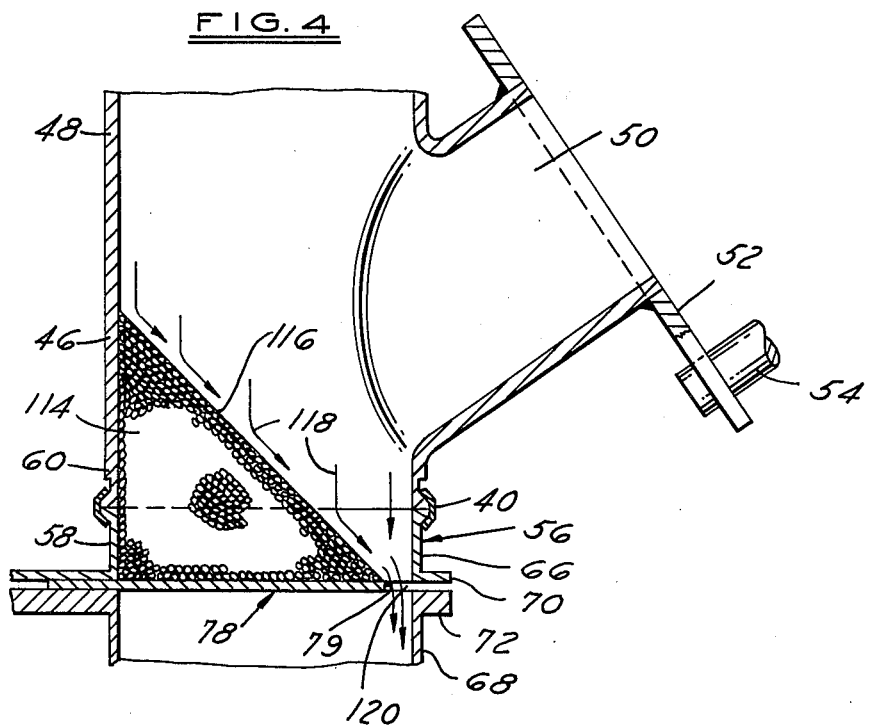
FIGS. 4 and 5 are fragmentary sectioned elevational views illustrating different modes of operation of the invention.
Figure 5:
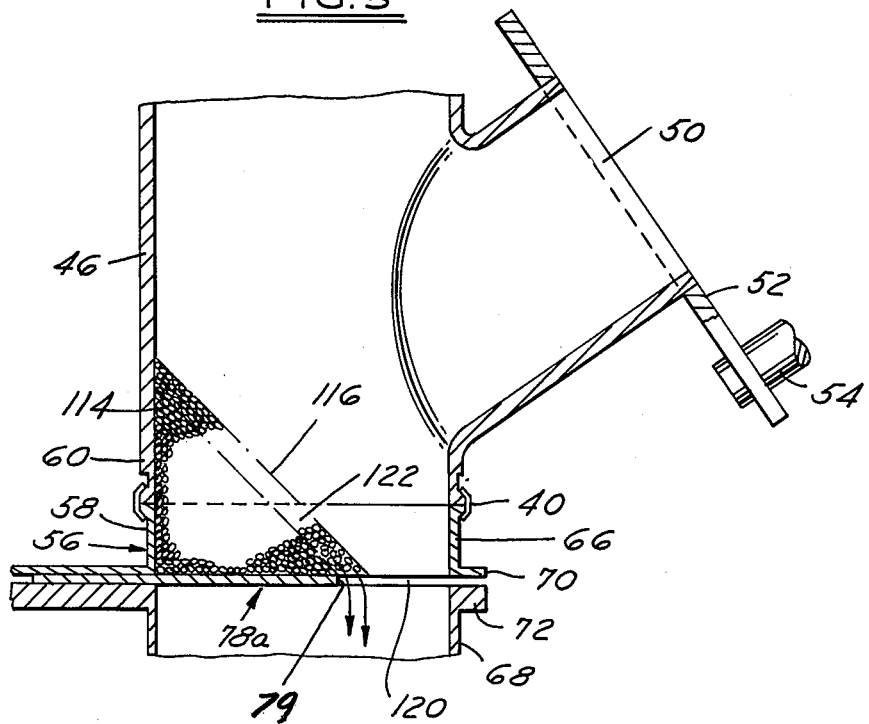

A material pulverizer 26 comprising a plurality of chopper blades 28 is carried within a second cylindrical conduit section 30, and a motor 32 is fixedly carried externally of section 30 and has a motor shaft 34 coupled to blades 28 through a bearing 36. Conduit section 30 has a vertical central axis and an upper input end 38 connected by the usual clamps (illustrated at 40 in FIGS. 4 and 5) to the lower end 42 of conduit 12. Pulverizer 26 operates when energized to pulverize, by chopping, beating and/or grinding, pelletized material received from conduit 12 into a smaller particulate size, thereby breaking open and subdividing the crust-encased pellets into particles the exterior surfaces of which are in larger part unencrusted, and simultaneously to at least partially mix the pulverized material particles to achieve a statistically uniform moisture distribution among the particles. Pulverized particulate material will flow by gravity through the lower end 44 of conduit section 30. A third cylindrical conduit section 46 is disposed below section 30 coaxially therewith and affixed thereto by a clamp 40 (FIG. 4), and has an upper end 48 which receives a particulate material stream from pulverizer 26 guided by a deflector 49 to impinge against the rear wall of conduit 46. A hollow cylindrical viewing window 50 opens into conduit section 46 at an angle with respect to the vertical conduit axis, as best seen in FIG. 4. A plate 52 is welded around the outside end of window 50 and has a mounting rod 54 extending therefrom parallel to but laterally displaced from the window axis. A fourth conduit section generally indicated at 56 is coaxially fastened at one end 58 by clamp 40 (FIG. 4) to the lower end 60 of section 46, and at a lower end 62 to a bent conduit 64 which directs particulate material flowing therethrough to a repelletization station or a waste container (not shown).

Conduit section 56 comprises first and second coaxially cylindrical sections 66, 68 having radially outwardly extending generally rectangular flange plates 70, 72 at the opposed ends thereof. As best seen in FIGS. 1 and 2, flange plates 70, 72 are affixed to each other by screws 74 with a collar 76 surrounding each screw 74 and spacing plates 70, 72 from each other. A shelf plate 78 (FIGS. 2 and 4) is mounted between flange plates 70, 72 over the head of a shoulder screw 80 received in lower plate 72, shelf plate 78 being held against radial movement by cooperation between the head of screw 80 and the corresponding hole in plate 78 received thereover and against axial movement by flange plates 70, 72. Screw 80 is accessible through an aligned hole in upper plate 70, as best seen in FIG. 2, for selectively removing shelf plate 78 without having to disconnect and remove the conduit sections, etc. A major portion (FIG. 2) of plate 78 projects through the material-confining wall defined by conduit sections 66, 68 in a direction perpendicular to the aligned central axes of the conduit sections. A pneumatic double-acting ram or electric bidirectional solenoid 82 is mounted at one end 84 by a pivot pin 86 to the brackets 88, 90 affixed by screws 92 to lower flange plate 72. Solenoid 82 has a plunger 94 which is pivotally connected by a coupler 95 and a pin 96 to a radially extending ear 98 on shelf plate 78. Thus, shelf plate 78 pivots in the plane of the plate about the axis of screw 80 upon energization of solenoid 82 through a range of positions, the first or maximum projected position being shown in solid lines in FIG. 2 wherein the edge 79 of plate 78 exposed in conduit 66, 68 is spaced from but disposed relatively close to the portion of the wall conduit closest to window 50.

First and second lengths 100, 102 of angle iron are mounted one upon another and fastened to upper flange plate 70 by screws 104 extending through slotted holes 106 in lengths 100, 102 and receiving corresponding nuts 108 (FIGS. 1 and 3). As best seen in FIG. 2, lengths 100, 102 extend in the direction of solenoid plunger 94 and have respective ends 101, 103 which cooperate with coupler 95 to limit axial movement of plunger 94 with respect to solenoid 82 and pivotal movement of coupler 95 about the axis of pin 86, and thereby to define respective inner and outer stops for coupler 95 corresponding to first and second positions of shelf plate 78, the second position of plate 78 and coupler 95 being illustrated in phantom at 78a, 95a in FIGS. 2 and 4. Lengths 100, 102 may be adjustably positioned axially with respect to coupler 95 and with respect to each other by means of slotted holes 106 selectively to define the location of first and second plate positions 78, 78a, the purpose of which will be described hereinafter.

An optical instrument case or head 110 (FIG. 1) is adjustably mounted to rod 54 by a clamp 112 and positioned to direct measurement beams through window 50 to the inside of conduit section 46. Head 110 may include suitable elements, such as a light source and a photocell, for affecting the desired material characteristic measurement. The components housed therein do not per se constitute part of the present invention. The head 110 shown for illustration in FIG. 1 is that used in moisture measurement apparatus heretofore marketed by applicant's assignee under the trademark "MR System". Briefly described, the "MR System" unit is designed to measure the moisture content of materials using a reflection/absorption measuring technique. A stabilized source of near-infrared light emits energy which is focused by a lens to an area or profile of about one square centimeter at the test material surface. Light reflected by the material is collected by the lens and directed onto a lead-sulphide photocell. A pair of narrow band interference filters are alternately passed through the reflected beam so that the photocell is alternately supplied with energy of a selected first wavelength sensitive to material moisture content and a selected second wavelength sensitive to material reflectivity but independent of moisture content. Head 110 may be connected to appropriate electronic circuitry to separate and compare the two signals, and thereby to yield an accurate indication of material moisture.

In the operation of the invention as thus far described, plate 78 is normally located in the first position illustrated in solid lines in FIGS. 2 and 4, such that plate edge 79 is spaced a given distance from an opposing portion of the conduit wall defined by aligned conduit section walls 66, 68 and located downstream of window 50. Initially, particulate material from pulverizer 26 (FIG. 1) falls upon shelf plate 78, and is collected and held stationary so as to pile up in the angle defined by plate 78 and conduit walls 46, 66, as illustrated by the pile built up at 114 in FIG. 4, to provide along the unbounded exposed surface of the pile a stationary material surface 116 exposed to impingement of falling particles thereon and inclined at an angle of material repose with respect to the shelf plate. Additional material in the material stream is deflected by deflector 49 and surface 116 to flow "downhill" along and over surface 116, as at 118 in FIG. 4, through the space 120 between plate edge 79 and the adjacent opposing conduit wall. Instrument head 110 measures an optical characteristic, specifically moisture content, of material 118 flowing downwardly over surface 116 against the optical backdrop or background provided by the underlying collected material 114. Thus, if a portion of the measurement beam illuminates surface 116 through a gap in deflected material 118, the resulting moisture measurement deviation will be substantially reduced if not eliminated.

To insure that the optical background provided by collected material surface 116 (FIG. 4) possesses a moisture content close to that of material 118 which is flowing thereover, a portion of the collected material is removed by energizing solenoid 82 (by means not shown) to retract plunger 94 (FIG. 2) periodically, i.e., after a selected number of readings by head 110. Plate 78 then pivots to the partially withdrawn second plate position 78a (FIGS. 2 and 5) and the layer 122 (FIG. 5) of material adjacent surface 116 spills through the enlarged gap 120 between the plate edge 80 and opposing conduit wall. Solenoid 82 is then energized in the opposite direction to return plate 78 to its first position (FIGS. 2 and 4). That portion of the previously-collected material not removed in the second plate position will collapse into the space adjacent conduit walls 46, 66, and fresh material from grinder 26 (FIG. 1) will be accumulated and held stationary to define material surface 116 (FIG. 4).

Head 110, assuming that it is of the type wherein the beam path generated therein is parallel to its longitudinal axis, is carried at a preferred angle of about fifty-five degrees with respect to the central axis of conduit section 46. The angle of material repose, with respect to horizontal and thus to plate 78 in the illustrated embodiment, will normally be between about thirty degrees for relatively coarse particulate material and about sixty degrees for finer particles, although an angle of repose of up to seventy degrees in some instances is envisioned. It has been found that best results are obtained when the radiant energy is focused to an area of about one square centimeter at the test material. Thus, head 110 is adjustably positioned on rod 54 by clamp 112 by measuring the distance between head 110 and surface 116 using a ruler or the like extending through window 50. The focal length is two hundred thirty (plus or minus twenty-five) millimeters in the case of the "MR System" head 110. The focal depth of field for the above-referenced "MR System" is about one centimeter. Thus, where a single material conveyor line and moisture measurement apparatus are to be used for different materials having widely varying angles of repose, the material surface for some materials may be outside of the preferred depth of field for the measurement beam for a particular first position of plate 78. For this reason, the first and second positions of plate 78 are made adjustable. The inserted first position for each material with which the apparatus 10 will be used is initially selected by trial and error to place the material surface 116 within the beam depth of field with the head 110 in a preselected fixed position. The retracted or second plate positions are selected for each material to insure that sufficient material will be removed from the pile to yield fresh material at the surface of the pile when the plate is reinserted to its first position. The corresponding positions of stop brackets 100, 102 for each material may be scribed or otherwise marked at appropriate locations so that the apparatus 10 thereafter may be adjusted by an unskilled operator for any of the selected materials or material types.

The embodiment of the invention hereinabove described in connection with FIGS. 1–5 is particularly useful and is preferred where the invention is to be used on a wide variety of materials having varying angles of repose requiring a relatively wide range of plate adjustment for laterally positioning the material surface. Where the invention is to be used with only one material, however, the alternative embodiment of the invention illustrated in FIGS. 6–11, wherein the general location of the material surface is "factory adjusted", is preferred. Referring to FIGS. 6–11, a shelf plate 130 is mounted by screws 132 onto a flat region machined into a shaft 134 which extends across a cylindrical conduit section 56a. Plate 130 is initially formed as a circular piece of flat sheet metal, such as stainless steel for example, and has one semicircular section 136 (best seen in FIG. 8) which extends from shaft 134 closely adjacent the inside wall of conduit section 56a. The second section 138 of plate 130 projects from shaft 134 and terminates in a peripheral edge 140 of generally elliptical contour which is specially formed to place the test surface of material collected on plate 130 within the depth of field of measurement head 110 (FIG. 1). Stated differently, plate edge 140 is specially formed to simulate a specific insertion depth of the plate 78 (FIGS. 2 and 4) for a particular material having a known or premeasured angle of repose. Edge 140 is spaced from the opposing inside wall of conduit section 56a in the first position of plate 130 illustrated in solid lines in FIG. 6 to define the material flow space 120 (FIGS. 6 and 8) for the purpose discussed above in connection with FIG. 4.

Opposite ends of shaft 134 project through diametrically opposed openings in conduit section 56a, and then through lip seals 142 and bearings 144 carried within hollow cylindrical bosses 146 externally welded on either side of the conduit section. A pivot arm 148 (FIGS. 6–8) encompasses one end 150 of shaft 134 which projects beyond the associated bearing 144 and is clamped thereto by a screw 152 which bridges a split 154 in the end of the arm. A key 156 (FIG. 6) is fitted into corresponding slots in arm 148 and shaft end 150 to insure corotation of the arm and shaft about the shaft axis. A solenoid 82 similar to that of FIGS. 1–5 is mounted at one end 84 by pivot pin 86 to brackets 88, 156, the latter of which is welded or otherwise affixed to conduit section 56a, as best seen in FIG. 7. Solenoid plunger 94 is connected by coupler 95 and pin 96 to an end of pivot arm 148 remote from shaft end 150.

The two angle brackets 160, 162 are mounted one upon another and adjustably secured to bracket 156 by the screws 164 extending through aligned slotted holes 166 in each bracket. Brackets 160, 162 have horizontally extending ends 168, 170 which axially capture coupler 95, plunger 94 extending through a slot 158 in bracket end 168 which is best seen in FIGS. 6, 10 and 11. Bracket ends 168, 170 cooperate with coupler 95 to limit axial travel of plunger 94 with respect to solenoid 82, and thereby to define upper and lower stops for coupler 95 respectively corresponding to second and first positions of shelf plate 130. In the second position of plate 130 illustrated in phanthom at 130a in FIG. 6 the plate is angulated slightly toward space 120 in the verticle direction of material flow. Thus, arm 148, shaft 134 and plate 130 pivot about the shaft axis upon energization of solenoid 82 between a first position adjustably defined by bracket 162 and a second position adjustably defined by bracket 160. In the first position, plate 130 is approximately horizontal, and material is collected thereon and illuminated as hereinabove described in connection with FIG. 4. The first plate position is made adjustable to "fine tune" the lateral position of the material surface at its angle of repose with respect to the depth of field of the measurement beam. When solenoid 82 is energized and plate 130 is pivoted to its second position 130a (FIG. 6), the collected material pile is tilted slightly and material adjacent the material surface spills therefrom through space 120. The plate is then returned to its first position at which fresh surface material is collected. It will be recognized that the embodiment of FIGS. 6–11, including conduit section 56a, may be used in place of the embodiment of FIGS. 1–5, including corresponding conduit section 56. One important advantage of the embodiment of FIGS. 6–11 is that the material flowing within conduit section 56a is sealed from the ambient.

Although the presently preferred embodiments of the invention has been described specifically in connection with the measurement of moisture content of pelletized material, many alternatives and modifications will be evident to the skilled artisan. For example, material characteristics other than moisture content could be measured. Where the bulk material in conveyor 14 (FIG. 1) is already in particulate form and has a uniform moisture distribution within each particle, i.e., where neither the pulverizing nor the mixing function of chopper 26 is required, such chopper may be deleted and bulk material may be fed directly from conveyor 14 to plate 78 (FIG. 4) or to plate 130 (FIG. 6). Similarly, the invention may be utilized with conveyor types other than screw conveyors 14 in FIG. 1, such as a pneumatic conveyor commonly used for grain products or the like, for example. Conduit 12 may project into the pneumatic conveyor line in such a modification to capture a sampling of material flowing therethrough.

All of the collected material on plate 78 may be removed by simply removing stop 102 (FIG. 2) to thereby allow plate 78 to be pivoted to a fully retracted third position. Similarly, all of the material may be removed from plate 130 (FIG. 6) by adjusting bracket end 168 to provide a stop when plate 130 is verticle. It has been found, however, that only a portion of the collected material need be removed under normal circumstances, as hereinabove described. Preferably, to save both energy and waste materials, pulverizer 26 is energized only periodically, thereby effecting a continuous sampling of material in conveyor 14 on a periodic basis. It will also be evident that the invention hereinabove described could be used to read the moisture content of material held stationary at surface 116 (FIG. 4) after pulverizer 26 (FIG. 1) has been turned off. Stated differently, the invention could be used to read the moisture content of a stationary material sample 114 (FIG. 4) without any material 118 flowing thereover. The technique hereinabove described is presently preferred because several moisture measurements may normally be taken without refreshing the collected background, whereas such background would have to be changed between each reading in the suggested modification. However, the invention is intended to embrace the above-noted and all other alternatives, modifications and variations as fall within the spirit and broad scope of the appended claims.

The invention claimed is:

1. A method of measuring a characteristic of particulate material flowing in a material stream comprising the steps of (a) positioning a shelf in said material stream at a first position such that a first quantity of material is accumulated and held stationary on said shelf to provide a material surface at an angle of repose with respect to said shelf, additional material in said stream flowing over said material surface, and (b) measuring said material characteristic by detecting at least one optical characteristic of said additional material flowing over said material surface.

2. The method set forth in claim 1 comprising the additional steps of: (c) periodically removing at least a portion of said first quantity of accumulated material adjacent said material surface, and (d) accumulating and holding stationary fresh material to provide said material surface.

3. The method set forth in claim 2 wherein said step (c) comprises the step of moving said self to a second position at which at least a portion of said first quantity of accumulated material is returned to said material stream and wherein said step (d) comprises the step of returning said shelf to said first position in said stream.

4. The method set forth in claim 3 comprising the additional step of adjusting said first position as a function of particle size.

5. The method set forth in claim 3 comprising the additional step of pulverizing material in said material stream such that relatively fine particulate materials are incident upon said shelf.

6. The method set forth in claim 2 wherein a bulk material stream is flowing generally horizontally and wherein sample material is taken from said bulk material stream and diverted to flow into a sample material stream, said material characteristic being measured in material flowing in said sample material stream, said method comprising the improved steps of taking said sample material from an upper portion of said bulk material stream.

7. The method set forth in claim 2 for use in measuring moisture content of pelletized material having an uneven moisture distribution within each material pellet, said method comprising the additional step of pulverizing and mixing said pelletized material such that relatively fine particulate material having surfaces exposed in an array providing a generally uniform moisture distribution within the material particles is incident upon said shelf.

8. Apparatus for optically measuring a preselected characteristic of particulate material flowing in a material stream comprising conduit means defining an enclosed material stream, shelf means disposed within said conduit means in said material stream for collecting and holding stationary within said conduit means a first quantity of material flowing in said stream to provide a stationary material surface within said conduit means at an angle of material repose with respect to said shelf means, and means disposed externally of said conduit means for measuring a said material characteristic by directing an optical beam from externally of said conduit means onto said material surface in said stream and detecting at least one optical material characteristic.

9. The apparatus set forth in claim 8 further comprising means for selectively removing at least a portion of said first quantity of material adjacent said material surface within said conduit means such that said portion of said first quantity of material is returned to said flowing material stream and fresh material is collected and held stationary on said shelf means internally of said conduit means to provide said material surface.

10. The apparatus set forth in claim 9 wherein material flowing in said stream in addition to said first quantity is deflected to flow over said material surface, and wherein said measuring means is adapted to detect at least one optical characteristic of said additional material deflected to flow over said material surface, said material surface providing a background for said optical beam.

11. The apparatus set forth in claim 8 wherein said means for measuring said material characteristic comprises means for focusing a said optical beam onto said material surface, said last-named means having a predetermined focal depth of field, and wherein said apparatus further comprises means coupled to said shelf means for adjustably positioning said material surface internally of said conduit means within said focal depth of field.

12. Apparatus for optically measuring a preselected characteristic of particulate material flowing in a material stream comprising shelf means disposed in said material stream for collecting and holding stationary a first quantity of material flowing in said stream to provide a stationary material surface at an angle of material repose with respect to said shelf means, material flowing in said stream in addition to said first quantity being deflected to flow over said material surface, means for measuring said material characteristic by directing an optical beam onto said material surface and detecting at least one optical material characteristic, said measuring means being adapted to detect at least one optical characteristic of said additional material deflected to flow over said material surface with said material surface providing a background for said optical beam, and means for selectively removing at least a portion of said first quantity of material adjacent said material suface such that fresh material is collected and held stationary on said shelf means to provide said material surface.

13. The apparatus set forth in claim 12 for measuring a said characteristic of particulate materials flowing in a confined material stream and comprising a conduit section disposed to confine a portion of said material stream and having a conduit section central axis, and wherein said shelf means is disposed adjacent a wall of said conduit section transversely of said central axis, said material collecting in the angle formed by said plate and said conduit wall.

14. The apparatus set forth in claim 13, wherein said shelf means comprises a plate disposed adjacent said conduit wall at a first plate position and being spaced from an opposing portion of said conduit wall, said material deflected to flow over said material surface flowing onwardly in said material stream through a space between said plate and said opposing wall section.

15. The apparatus set forth in claim 14 wherein said means for removing at least a portion of said material comprises means for moving said plate to a second plate position such that at least a portion of said collected material adjacent said material surface is dislodged therefrom to flow onwardly in said material stream through an enlarged space defined between said plate in said second position and said opposing wall section.

16. The apparatus set forth in claim 15 wherein said plate is disposed to project through said conduit wall into said material stream in said first plate position and to be at least partially withdrawn from within said conduit section in said second plate position.

17. The apparatus set forth in claim 16 wherein said shelf means further comprises means mounting said plate to pivot about an axis generally parallel to said central axis between said first and said second plate positions.

18. The apparatus set forth in claim 15 further comprising means for adjustably selecting both said first and second plate positions.

19. The apparatus set forth in claim 15 wherein said central axis of said conduit section is disposed in the vertical direction, and wherein said material flows by gravity over said material surface.

20. The apparatus set forth in claim 15 wherein said conduit section further comprises an optical window, and wherein said measuring means is disposed externally of said conduit section and directs said optical beam onto said material surface through said optical window.

21. The apparatus set forth in claim 15 wherein said plate is mounted within said conduit section to pivot about an axis transverse to said central axis between a said first position generally transverse to said central axis and a said second position angulated in the direction of material flow toward said space.

22. The apparatus set forth in claim 21 wherein said apparatus further comprises a shaft extending transversely across said conduit section, said plate being carried by said shaft, and means for conjointly pivoting said shaft and plate between said first and second positions.

23. The apparatus set forth in claim 22 wherein said conduit section is substantially cylindrical, and wherein said plate is substantially flat and has a semicircular first plate edge extending from said shaft adjacent said conduit wall and a generally elliptical second plate edge extending from an opposite side of said shaft and spaced from said opposing conduit wall section.

24. The apparatus set forth in claim 12 for measuring moisture content of pelletized material having an uneven moisture distribution within each material pellet said apparatus further comprising means disposed in said material stream to reduce said pelletized material into a smaller particle size prior to incidence of said particulate material onto said shelf means.

25. The apparatus set forth in claim 24 wherein said pellet reducing means is disposed such that its output is directed in a stream flowing onto said material surface.

26. Apparatus for optically measuring a preselected characteristic of particulate material flowing in a material stream comprising shelf means disposed in said material stream for collecting and holding stationary a first quantity of material flowing in said stream to provide a stationary material surface at an angle of material repose with respect to said shelf means, material flowing in said stream in addition to said first material being deflected to flow over said surface, and means for measuring the said material characteristic of said additional material deflected to flow over said material surface by directing an optical beam onto said material surface and detecting at least one optical material characteristic of said additional material with said material surface providing a background for said optical beam.

* * * * *